(12) United States Patent
Shiraki et al.

(10) Patent No.: US 7,719,303 B2
(45) Date of Patent: May 18, 2010

(54) LIQUID CRYSTAL DISPLAY DEVICE AND ANALYSIS DEVICE INCLUDING THE SAME

(75) Inventors: Yasunori Shiraki, Kyoto (JP); Takuji Kawai, Kyoto (JP); Yoshimi Oura, Kyoto (JP)

(73) Assignee: Arkray, Inc., Kyoto (JP)

( * ) Notice: Subject to any disclaimer, the term of this patent is extended or adjusted under 35 U.S.C. 154(b) by 70 days.

(21) Appl. No.: 11/629,175

(22) PCT Filed: Jun. 29, 2005

(86) PCT No.: PCT/JP2005/011922

§ 371 (c)(1),
(2), (4) Date: Dec. 11, 2006

(87) PCT Pub. No.: WO2006/003919

PCT Pub. Date: Jan. 12, 2006

(65) Prior Publication Data

US 2008/0074136 A1     Mar. 27, 2008

(30) Foreign Application Priority Data

Jul. 6, 2004     (JP) .............................. 2004-199728

(51) Int. Cl.
*G01R 31/00* (2006.01)
(52) U.S. Cl. ..................................... 324/770
(58) Field of Classification Search .................. 324/770
See application file for complete search history.

(56) References Cited

U.S. PATENT DOCUMENTS

| 4,311,993 | A | 1/1982 | Strobel |
| 5,379,238 | A * | 1/1995 | Stark ........................... 703/11 |
| 5,812,102 | A | 9/1998 | Sprole, Jr. et al. |
| 7,404,796 | B2 * | 7/2008 | Ginsberg .................... 600/365 |
| 2004/0048394 | A1 * | 3/2004 | Kirchhevel ................... 436/183 |
| 2006/0279321 | A1 * | 12/2006 | Ruppender et al. .......... 324/770 |

FOREIGN PATENT DOCUMENTS

| CN | 1300025 A | 6/2001 |
| EP | 0 854 424 A1 | 7/1998 |
| EP | 0 854 424 B1 | 5/2003 |
| EP | 1 538 588 A2 | 6/2005 |
| GB | 2 277 418 A | 10/1994 |
| JP | 07-128338 | 5/1995 |
| JP | 2000-214423 | 8/2000 |
| JP | 2004-045763 | 2/2004 |

* cited by examiner

*Primary Examiner*—Ha Tran T Nguyen
*Assistant Examiner*—Shaun Campbell
(74) *Attorney, Agent, or Firm*—Global IP Counselors, LLP (57) ABSTRACT

In order to provide a liquid crystal display device which can detect a defective indication due to short circuit which occurs between a common electrode and a counter electrode by a conductive impurity enters into a liquid crystal display panel, and an analysis device including the same, a blood glucose meter includes a display section and a microcomputer. For performing an inspection for a defective indication on a liquid crystal display panel of the display section, the microcomputer uses ports as input/output ports for a defective indication inspection. The microcomputer detects whether an inspection signal sent from the port can be received at the other port or not to perform the inspection for a defective indication.

3 Claims, 6 Drawing Sheets

LIQUID CRYSTAL DISPLAY DEVICE AND ANALYSIS DEVICE INCLUDING THE SAME

TECHNICAL FIELD OF THE INVENTION

The present invention relates to a liquid crystal display device of a segment method, dot matrix method, or the like, which displays numerals and texts, and an analysis device including the same.

BACKGROUND OF THE INVENTION

Recently, liquid crystal display devices are incorporated into a variety of electronic equipment, such as clocks, calculators, analysis devices, home electric appliances and the like as display sections.

For example, one type of a liquid crystal display device which displays simple indication such as numerals and texts is a liquid crystal display device of a segment method. The liquid crystal display device of the segment method includes a common electrode which is formed on one of two substrates, a plurality of segmented electrodes which are patterned into the shape of numerals on the other substrate, and a liquid crystal enclosed between the two substrates. A voltage is applied between the common electrode and the segmented electrodes, and an orientation of the liquid crystal enclosed therebetween is changed to control transmission of light. In this way, texts and numerals can be displayed.

SUMMARY OF THE INVENTION

Problems to be Solved by the Invention

However, the above conventional liquid crystal display device has the following problems.

In the liquid crystal display device of the segment method as disclosed in Japanese Laid-Open Publication No. 7-128338, if a conductive impurity enters between the above-described common electrode and the segmented electrodes, a short circuit occurs between the common electrode and the segmented electrodes. A difference in potential is lost, and an appropriate indication cannot be displayed (see FIGS. 5A and 5B). Even though such a defective indication is not observed when the product is manufactured, it may suddenly appear while in use for some reason. Thus, an inspection of a defective indication at the shipping of products is hardly sufficient as the measures to address such a problem.

Moreover, if such a defective indication appears in a liquid crystal display device incorporated in a blood glucose meter which is used by a diabetic patient for measuring a blood glucose level by oneself, the diabetic patient or the like may not notice that the wrong indication is displayed. Blood glucose level control by an injection of insulin or the like conducted in accordance with the erroneously displayed blood glucose level is not an appropriate treatment for the patient who measures the blood glucose level. Particularly, many of the people who take blood, such as diabetic patients, are elderly or visually handicapped people. Thus, it can be expected that they do not notice the defective indication of the liquid crystal display device. However, the conventional liquid crystal display devices incorporated in the blood glucose meters do not include means for detecting defective indication, or means for notifying the defective indication in particular.

An object of the present invention is to provide a liquid crystal display device which can detect a defective indication which appears due to a short circuit between a common electrode and a counter electrode thereof caused by a conductive impurity entering into a liquid crystal display panel, and an analysis device including the same.

Means for Solving the Problems

A liquid crystal display device according to the invention includes a liquid crystal display panel, an input and output section, and a control section. The liquid crystal display panel includes a first substrate with a first electrode formed thereon, a second substrate with a common electrode formed thereon and a liquid crystal enclosed between the first substrate and the second substrate. The liquid crystal display panel displays by changing an orientation of the liquid crystal by a difference in potential applied between the first electrode and the common electrode. The input and output section has a first output terminal and a second output terminal configured to drive the liquid crystal display panel. The first output terminal sends a signal to the first electrode. The second output terminal sends a signal to the common electrode.

The control section uses the first output terminal and the second output terminal of the input and output section as input and output terminals for a defective indication inspection configured to perform an inspection for a defective indication in the liquid crystal display panel. The control section performs the inspection for a defective indication by detecting whether a signal sent from one of the input and output terminals of the input and output section can be received at the other of the input and output terminals.

With such a structure, the first output terminal and the second output terminal which are respectively connected to the first electrode side and the common electrode side opposing the first electrode and which are used as output terminals for driving the liquid crystal when a normal indication is displayed are used as the input and output terminals for the defective indication inspection to perform an inspection for a defective indication in the liquid crystal display panel. During the defective indication inspection, if the signal sent from the one input and output terminal is received at the other input and output terminal, the control section detects an presence of a defective indication.

In such a structure, when a conductive impurity enters between the common electrode and the opposing first electrode, a short circuit occurs between the common electrode and the first electrode and a difference in potentials is lost. Thus, an appropriate indication cannot be displayed.

Thus, for detecting such the presence of a defective indication, the liquid crystal display device of the present invention uses the output terminal on the first electrode side and the output terminal on the common electrode side which are used as output terminals for driving the liquid crystal when a normal indication is displayed are used as the input and output terminals for the defective indication inspection. Then, whether the signal sent from one input and output terminal can be received at the other input and output terminal or not is checked. If the signal can be received at the other input and output terminal, it means that there is a conductive impurity which connects the first electrode and the common electrode in the liquid crystal.

In this way, by only using the output terminals (on the first electrode side and the common electrode side) for driving the liquid crystal are used as the input and output terminal for the inspection to detect that the signal sent from one input and output terminal is received at the other input and output terminal, the defective indication due to a short circuit caused in the liquid crystal display device can be readily detected.

The first electrode mentioned above corresponds to a segmented electrode in a liquid crystal display device of a segment method, and to a counter electrode formed on a first substrate at a position which corresponds to dots in a liquid crystal display device of a dot matrix method.

A liquid crystal display device according to the invention is a liquid crystal display device according to the teachings of the invention in which the control section displays a message notifying that a defective indication appears on the liquid crystal display panel when the control section detects the defective indication.

With such a structure, when an appearance of a defective indication is detected, for example, a text saying that defective indication is appearing is displayed on the liquid crystal display panel, lamp is lit, a displayed numerals are flickered, or the like.

In this way, it becomes possible to surely notify the user that the current indication is not correctly displayed. Thus, a diabetic patient can be prevented from conducting blood glucose control in reliance on the erroneously displayed blood glucose measured value.

A liquid crystal display device according to the invention is a liquid crystal display device according to the teachings of the invention in which the control section sounds an alarm sound when it detects the defective indication.

With such a structure, an alarm sound is sounded when the presence of a defective indication is detected. In this way, it becomes possible to surely notify the user that the current indication is not correctly displayed.

Accordingly, a diabetic patient or a visually handicapped person can be prevented from conducting blood glucose control in reliance on the erroneously displayed blood glucose measured value.

A liquid crystal display device according to claim 4 is a liquid crystal display device according to claim 1 in which the control section stops displaying on the liquid crystal display panel when it detects the defective indication.

With such a structure, when the control section detects a defective indication, the device is controlled to stop displaying the numerical values or the like on the liquid crystal display panel.

In this way, visually handicapped patients such as elderly people can be securely prevented from conducting blood glucose control in reliance on the erroneously displayed blood glucose measured value. Thus, a liquid crystal display device with higher safety can be provided.

A liquid crystal display device according to claim 5 is a liquid crystal display device according to any one of claim 1 in which the control section performs the inspection for a defective indication every time power is turned on, and/or the display is switched.

With such a structure, the inspection for the defective indication is performed every time when the power is turned on before displaying or the display is switched.

In this way, in the liquid crystal display section incorporated in the blood glucose meter, the inspection for a defective indication is performed every time when the power is turned on before displaying or the display is switched. When a defective indication appears, measures such as notifying by an alarm sound is taken. Thus, it becomes possible to prevent the user from believing in the displayed numeral to be correct in the case of appearance of the defective indication.

An analysis device according to the invention includes a liquid crystal display device according to the teachings of the invention as a display section.

With such a structure, the liquid crystal display device of the present invention can be used as, for example, a display section of an analysis device such as blood glucose meter.

In this way, the presence of a defective indication caused by a conductive impurity enters into a liquid crystal layer can be detected and notified to the user. Thus, it becomes possible to prevent the user from believing in the displayed numeral to be correct in the case of appearance of the defective indication and conducting wrong treatment such as performing inappropriate blood glucose control or the like.

FUNCTION OF THE INVENTION

According to the liquid crystal display device of the invention, the presence of a defective indication caused by a conductive impurity enters into a liquid crystal layer can be detected.

According to the liquid crystal display device of the invention, it becomes possible to surely notify the user that the current display is not correct.

According to the liquid crystal display device of the invention, a user can be prevented from performing blood glucose level control in reliance of an erroneously displayed blood glucose measure value.

According to the liquid crystal display device of the invention, a visually handicapped patient such as an elderly person can be securely prevented from performing blood glucose level control in reliance of an erroneously displayed blood glucose measure value.

According to the liquid crystal display device of the invention, when a defective indication appears, measures such as notifying by an alarm sound can be taken.

According to the analysis device of the invention, the presence of a defective indication caused by a conductive impurity enters into a liquid crystal layer can be detected.

DESCRIPTION OF THE REFERENCE SYMBOLS

10 blood glucose meter
11 display section (liquid crystal display device)
12 sensor section
12a sensor
15 microcomputer (control section, liquid crystal display device)
15a first port (first output terminal, input and output terminal, input and output section)

15b second port (second output terminal, input and output terminal, input and output section)
16 alarm section
17 power supply section
SEG segmented electrode
COM common electrode

DETAILED DESCRIPTION OF THE INVENTION

A blood glucose meter (analysis device) 10 including a display section (liquid crystal display device) 11 according to an embodiment of the present invention is described as follows with reference to FIGS. 1 through 6.

Structure of Entire Blood Glucose Meter

Figure 1:
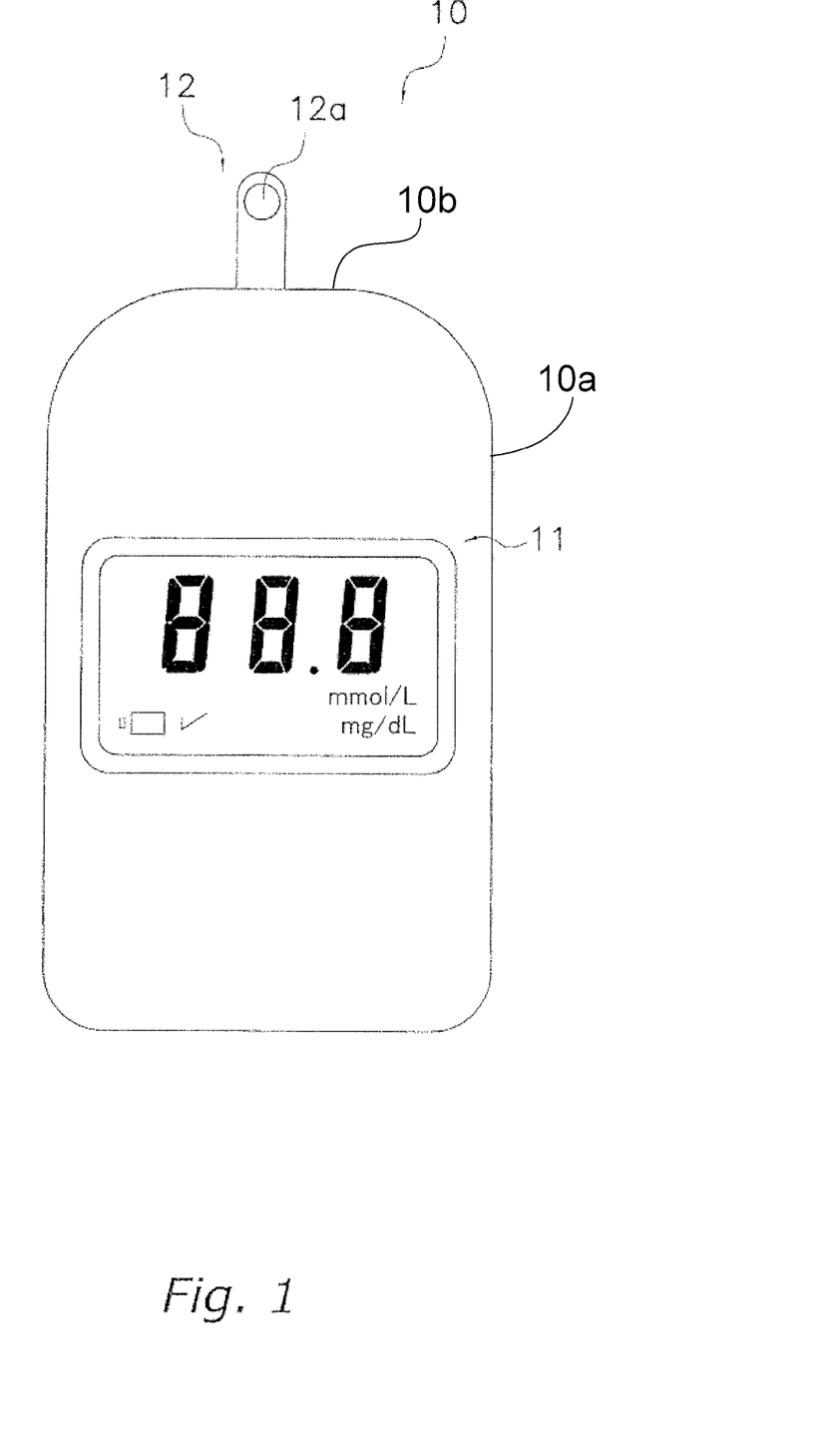
FIG. 1 is a front view showing a blood glucose meter as an example of an analysis device which includes a liquid crystal display device of the present invention as a display section.
Figure 2A:
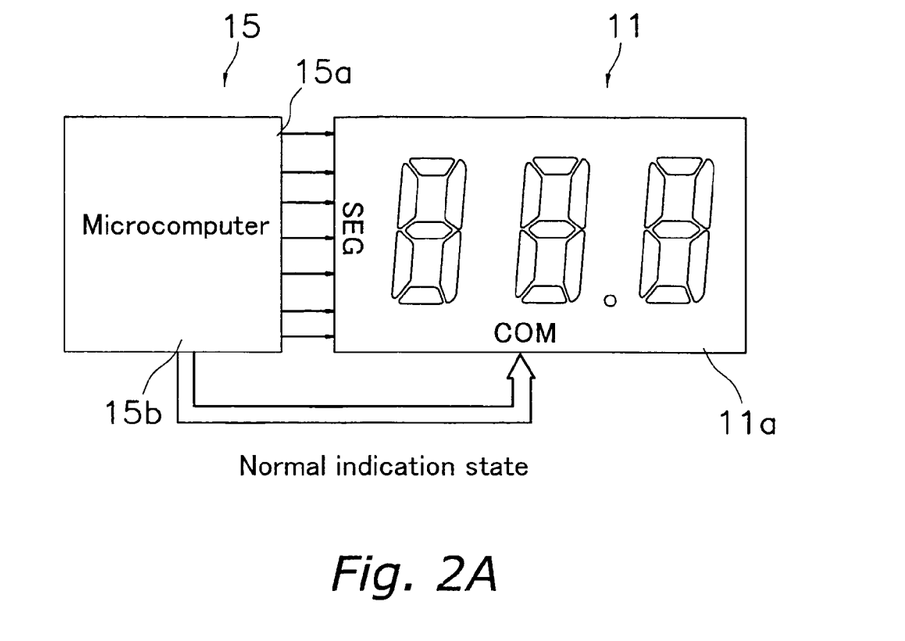
FIG. 2A is a diagram showing a normal indication state of the blood glucose meter of FIG. 1.

As shown in FIG. 1, the blood glucose meter 10 according to the present embodiment is a blood glucose measurement device that includes a case 10a with a top end 10b, the display section (liquid crystal display device) 11, and a sensor section 12, and also incorporates a microcomputer (control section) 15 (see FIG. 2) inside.

The display section 11 is a liquid crystal display device of a segment method which displays a blood glucose level measured by depositing blood on the sensor section 12. As shown in FIG. 1, the display section 11 displays a numerical value to two places to the left to the decimal point and one place to the right of the decimal point (result of measurement of the blood glucose level). The display section 11 also displays a remaining battery life of the blood glucose meter 10, and the like. A normal indication of the display section 11, an inspection of a defective indication, and the like will be described later in details.

The sensor section 12 is a fixed projection that extends in a longitudinal direction from the top end 10b of the case 10a of the blood glucose meter 10, as shown in FIG. 1. The sensor section 12 is basically a rigid protrusion that includes a sensor 12a at a distal end thereof for depositing a blood flowed from a puncture wound formed by a lancet or the like for measuring the blood glucose level at a predetermined position of its tip portion. The blood deposited on the sensor 12a is analyzed, and the blood glucose level is measured.

The microcomputer 15 is a microcomputer of an internal LCD driver type which drives a liquid crystal of the display section 11. As shown in FIG. 2A, the microcomputer 15 includes ports (input and output section which are the first and second output terminals) 15a and 15b which are connected to an SEG (segmented electrode which is the first electrode) and a COM (common electrode) of the display section 11. The microcomputer 15 uses the ports 15a and 15b as ports of the LCD driver for driving the liquid crystal of the display section 11 during normal indication. How the ports 15a and 15b are handled by the microcomputer 15 in the inspection for a defective indication will be described later in details.

Structure of Display Section

Figure 2B:
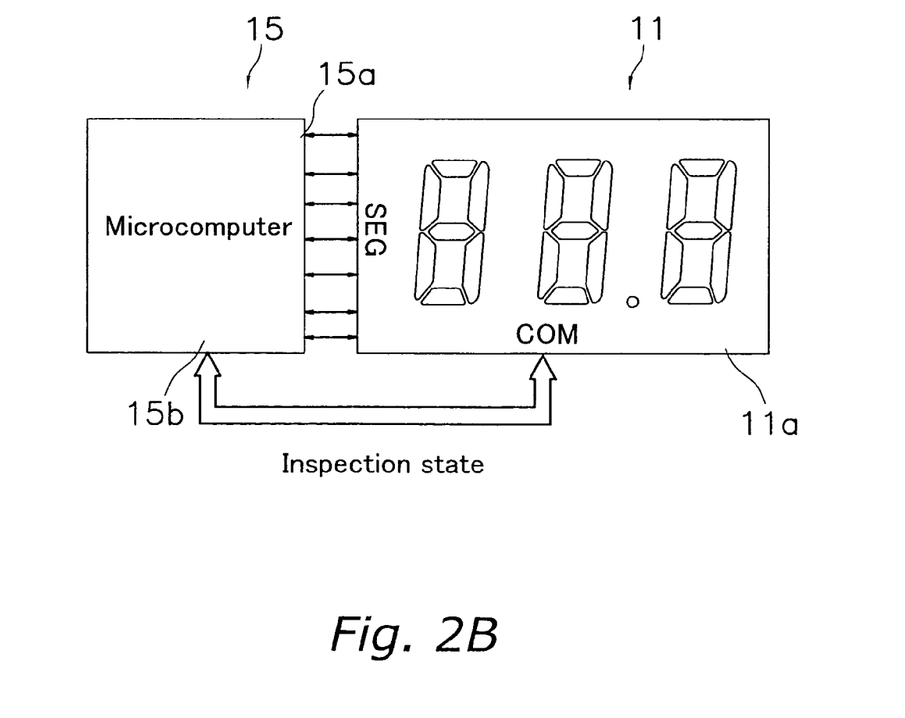
FIG. 2B is a diagram showing an inspection state for a defective indication.

As shown in FIG. 1, the display section 11 includes a liquid crystal display panel 11a. Furthermore, as shown in FIGS. 2A and 2B, the display section 11 includes the SEG formed on one of the substrates which form the liquid crystal display panel 11a of the display section 11, and the COM formed on the other substrate. By applying a voltage between the SEG and the COM, an alignment of the liquid crystal enclosed between the two substrates is changed. Thus, segmented portions are respectively switched between a displaying state and a non-displaying state.

The SEG is a segmented electrode patterned on one substrate as seven segments for displaying numerals. The COM is an electrode formed across a surface of the other substrate.

The SEG and the COM are connected to the ports 15a and 15b of the microcomputer 15 which functions as the ports of the LCD driver. The SEG and the COM receive a signal (voltage) sent from the microcomputer 15 in accordance with the result of measuring the blood glucose level. Thus, a difference in potentials is generated between the SEG and the COM, and the alignment of the liquid crystal between the SEG and the COM required for displaying a desired numeral is changed to display the blood glucose level.

Now, a case of a defective indication caused by an impurity trapped in the liquid crystal display panel 11a of the display section 11 is described.

As described above, a numeral is displayed on the display section 11 by generating a difference in potentials between the SEG and the COM. However, when a conductive impurity enters between the SEG and the COM, the potential difference between the SEG and the COM is lost. Thus, in the segmented portions where the alignment of the liquid crystal should be changed for display, the alignment of the liquid crystal remains unchanged, causing the portions not to be displayed. This results in a defective indication (see FIGS. 5A and 5B).

Figure 5A:
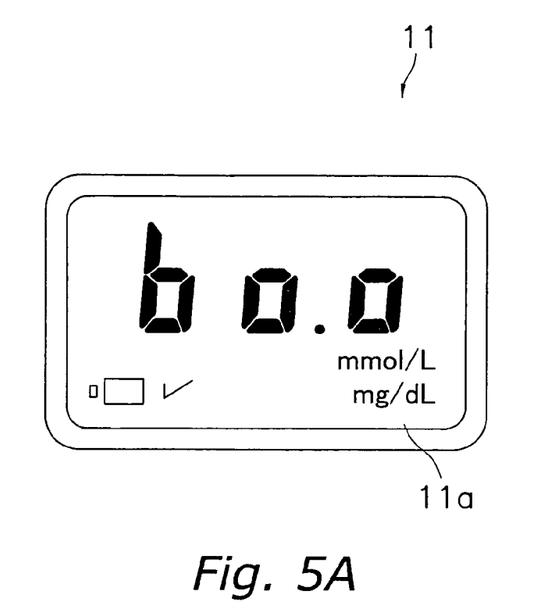
FIGS. 5A and 5B are diagrams showing a display section with a defective indication.

When such a defective indication appears in a liquid crystal display device used as the display section 11 of the blood glucose meter 10 as in the present embodiment, a user may misunderstand that the numerals erroneously displayed is a correct measurement result, and inject insulin for blood glucose control based on the wrong measured value. Such a wrong blood glucose control is just an inappropriate treatment for a diabetic patient. Rather, it may be harmful for the patient. Particularly, many of the diabetic patients who use the blood glucose meter 10 as in the present embodiment have weak eyesight. They may falsely recognize the defective indication as shown in FIG. 5A to be "60.0", for example, without noticing that it is a defective indication.

Thus, in the blood glucose meter 10 of the present embodiment, in order to prevent an inappropriate treatment caused by misunderstanding of the user, a defective indication is checked for every time the blood glucose meter 10 is powered on and/or the display is switched, and, when the appearance of a defective indication is detected, the user is notified of the appearance of the defective indication.

Structure of Microcomputer

Figure 6:
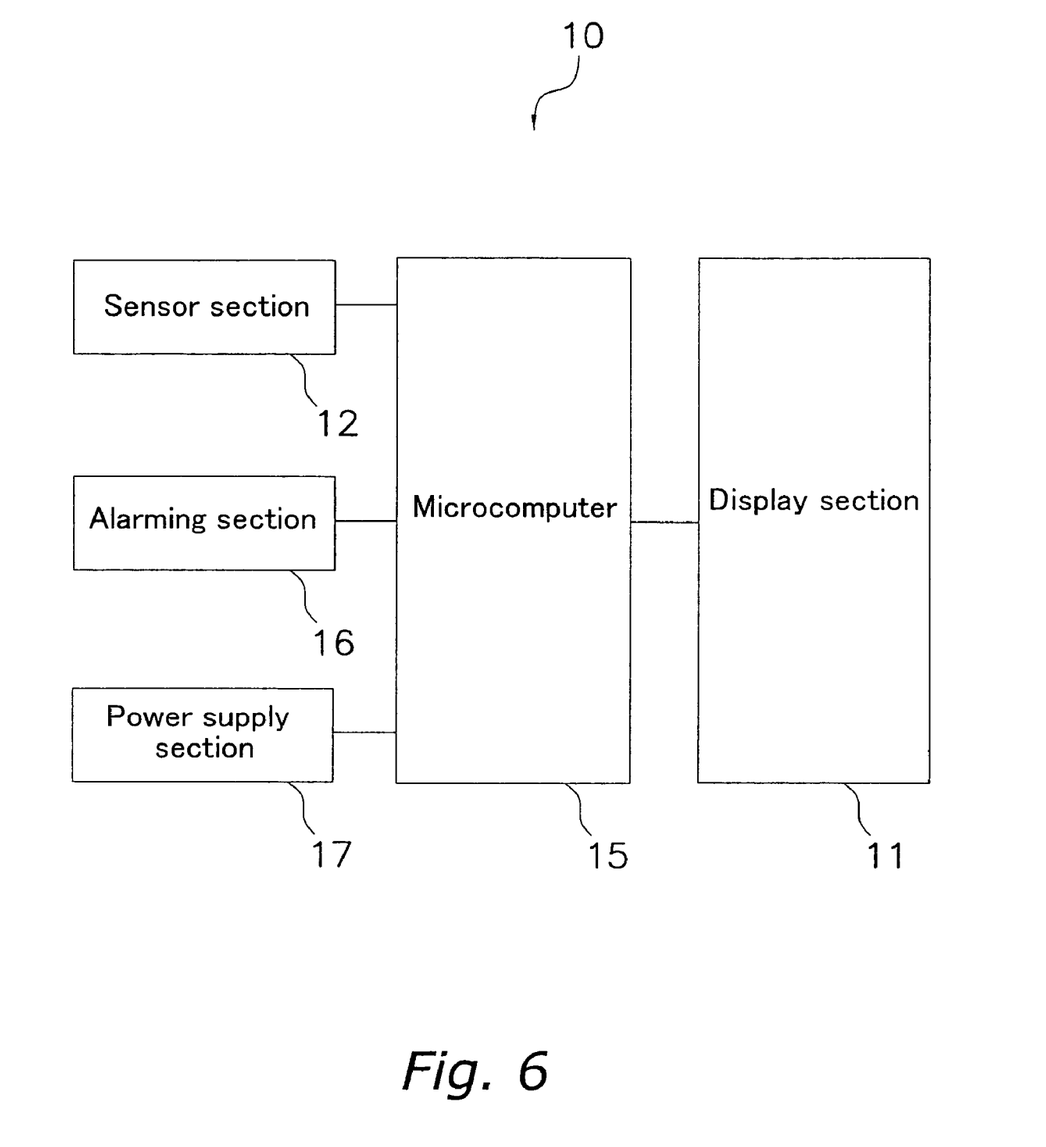
FIG. 6 is a block diagram showing a connection state with a microcomputer incorporated in the blood glucose meter of FIG. 1.

As shown in FIGS. 2A and 2B, the microcomputer 15 includes the port 15a connected to the SEG side of the display section 11 and the port 15b connected to the COM side. Furthermore, as shown in FIG. 6, the microcomputer 15 is connected to the display section 11, the sensor section 12, an alarm section 16, and a power supply section 17.

For a normal indication, in the microcomputer 15, a signal (voltage) is sent from the port 15a to the SEG corresponding to the segments to be displayed based on the blood glucose level measured at the sensor section 12. To the COM side, a signal (voltage) is sent from the port 15b at a timing of displaying.

The microcomputer 15 also performs various types of controlling operations such as checking for a defective indication which appears when a conductive impurity enters into the liquid crystal display panel 11a, analyzing the blood detected at the sensor section 12 and calculating the blood glucose level, and the like, in addition to drive control of the liquid crystal display panel 11a of the display section 11.

As shown in FIG. 2B, specifically, the inspection for a defective indication is performed using the ports 15a and 15b used as output terminals of the LCD driver as I/O ports (input and output terminals) for the defective indication inspection.

The alarm section 16 sounds a buzzer to notify the user that the currently displayed numerical value is a wrong indication when the microcomputer 15 detects a defective indication in the inspection for the defective indication.

The power supply section 17 which supplies power to electronic equipment incorporated in the blood glucose meter 10 stops the power supply to the display section 11 when the microcomputer 15 detects a defective indication.

An Inspection Method of the Present Blood Glucose Meter

An inspection method for a defective indication in the blood glucose meter 10 of the present embodiment is described as follows with reference to FIGS. 3a through 4B.

Figure 3A:
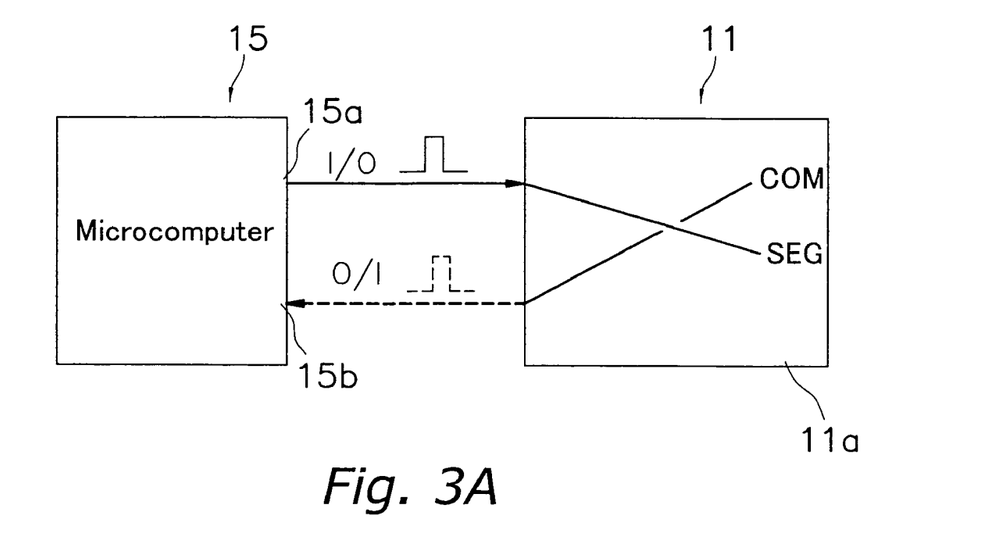
FIGS. 3A and 3B are diagrams showing how an inspection signal is sent and received when there is no defective indication.
Figure 3B:
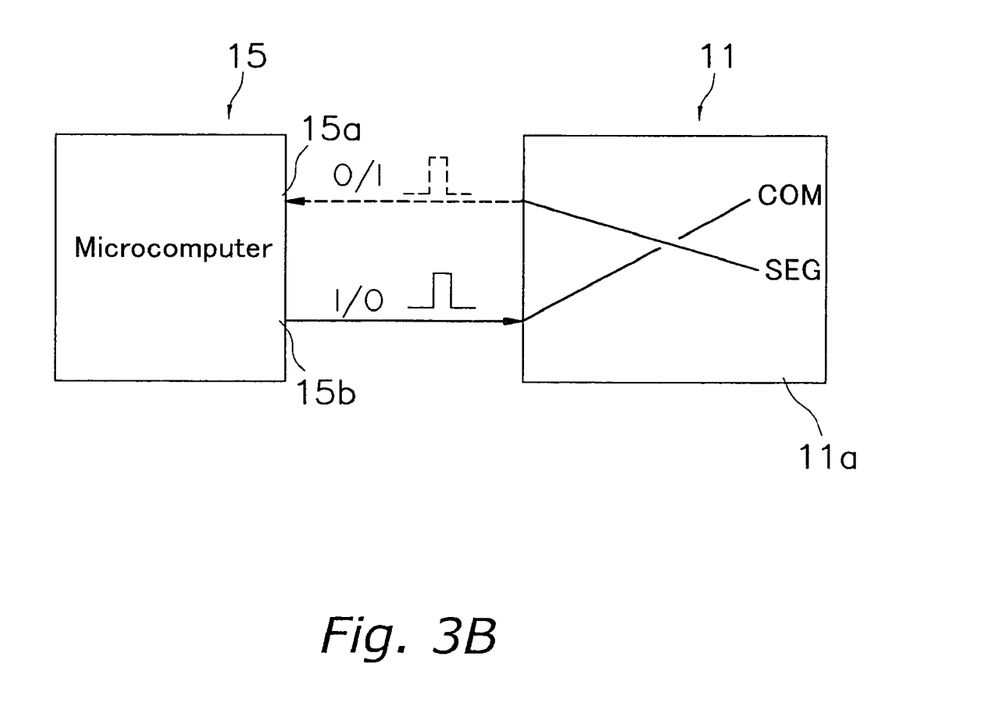

In the blood glucose meter 10 of the present embodiment, every time the power is turned on, and/or the display is switched, the microcomputer 15 uses the ports 15a and 15b as the I/O ports. As shown in FIG. 3A, an inspection signal is sent from one of the ports, the port 15a, which is connected to the SEG. Whether the inspection signal can be received or not at the other port, the port 15b which is connected to the COM, is checked. In other words, whether there is a short circuit between the SEG and the COM of the liquid crystal display panel 11a is checked. Such an inspection is performed between all the SEGs and the COMs. Alternatively, as shown in FIG. 3B, the inspection signal may be sent from the other port 15b and whether the inspection signal can be received or not at the one port 15a may be checked.

Figure 4A:
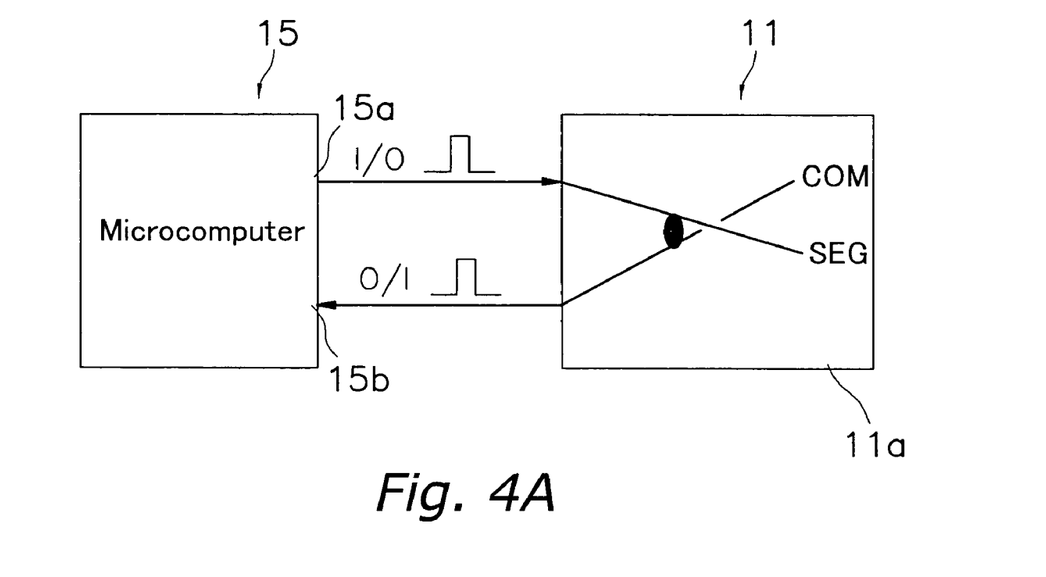
FIGS. 4A and 4B are diagrams showing how an inspection signal is sent and received when a defective indication appears.
Figure 4B:
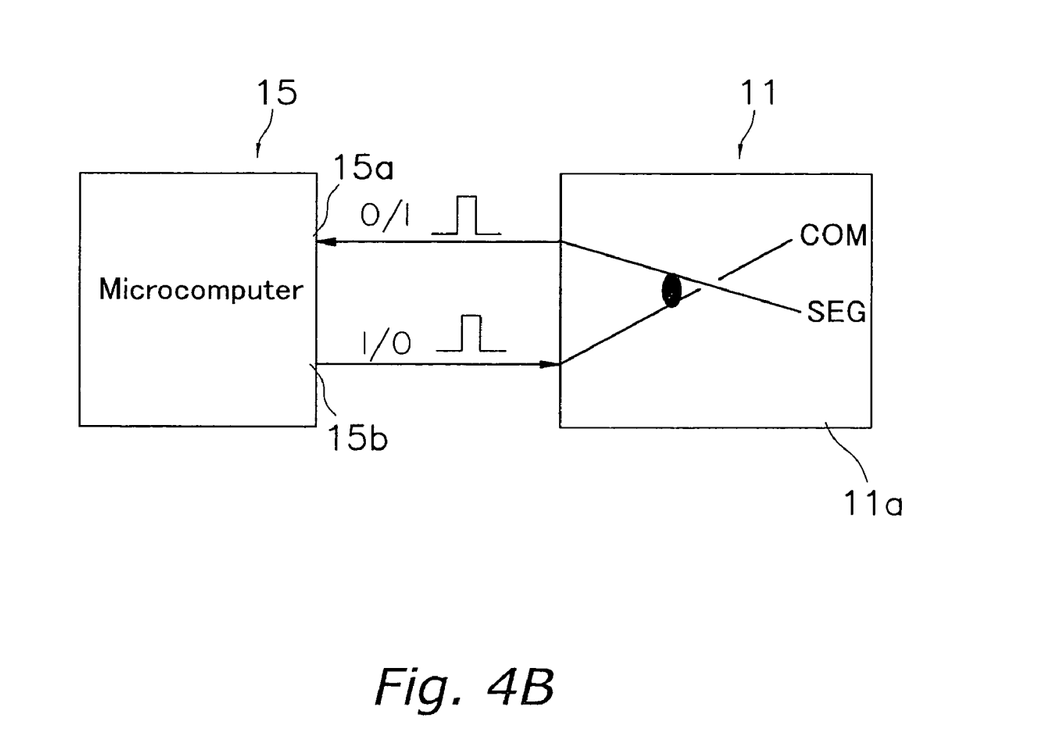
Figure 5B:
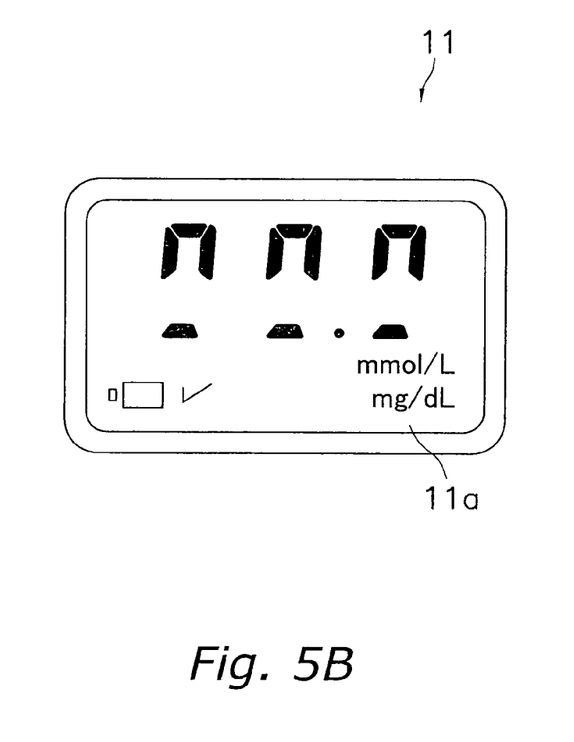

If there is an impurity trapped between the SEG and the COM of the liquid crystal display panel 11a and there is short-circuit as shown in FIGS. 4A and 4B, the difference in potentials between the SEG and the COM is lost, and the alignment of the liquid crystal cannot be changed. Thus, the segmented portions which should be displayed cannot be displayed, and a defective indication as shown in FIGS. 5A and 5B may appear.

In the blood glucose meter 10 of the present embodiment, when appearance of such a defective indication is detected, the inspection signal sent from the one port 15a is detected at the other port 15b as shown in FIG. 4A since there is a short circuit between the SEG and the COM of the liquid crystal display panel 11a. The same is also true of the case where the inspection signal sent from the other port 15b is detected at the one port 15a as shown in FIG. 4B.

When the inspection signal sent from the port 15a or the port 15b is received at the port 15b or the port 15a, the microcomputer 15 controls the alarm section 16 to sound a buzzer. Further, the microcomputer 15 has the liquid crystal display panel 11a of the display section 11 to display a message notifying that a defective indication is present.

In this way, it becomes possible to surely notify the user that a defective indication appears and the numeral displayed on the liquid crystal display panel 11a is wrong.

Features of the Present Blood Glucose Meter (1)

The blood glucose meter 10 of the present embodiment includes the display section 11, the microcomputer 15, and the like. The ports 15a and 15b used as the output terminals of the LCD driver when a normal indication is displayed are used as the I/O ports for the inspection when the inspection for a defective indication is performed. In a use as the I/O ports, for example, an inspection signal is sent from the one port 15a which is connected to the SEG of the liquid crystal display panel 11a. If the inspection signal is received at the other port 15b which is connected to the COM of the liquid crystal display panel 11a, the microcomputer 15 detects the presence of a defective indication.

In this way, it is ensured that a defective indication due to a short circuit caused by an impurity trapped between the SEG and the COM of the liquid crystal display panel 11a is detected. As a result, it becomes possible to prevent treatment such as wrong blood glucose control due to a defective indication appearing on the blood glucose meter 10 which is used by diabetic patients including a number of visually handicapped elderly people.

(2)

In the blood glucose meter 10 of the present embodiment, when the appearance of the defective indication as described above is detected, the microcomputer 15 has the display section 11 to display a message notifying of the "presence of a defective indication".

In this way, it becomes possible to ensure notifying the user of the appearance of the defective indication. As a result, problems such as conducting inappropriate treatment in reliance on an erroneously displayed numerical value can be avoided.

(3)

In the blood glucose meter 10 of the present embodiment, when the appearance of the defective indication as described above is detected, the microcomputer 15 controls the alarm section 16 to sound a buzzer.

In this way, it becomes possible to further ensure notifying the user of the existence of the defective indication. As a result, problems such as conducting inappropriate treatment in reliance on an erroneously displayed numerical value can be avoided.

As in the present embodiment, a plurality of warning means, such as displaying a message notifying of a defective indication, an alarm by a buzzer and the like may be combined.

(4)

In the blood glucose meter 10 of the present embodiment, the inspection for a defective indication as described above is performed every time the power of the blood glucose meter 10 is turned on, and/or the display is switched.

In this way, basically, whether there is the presence of a defective indication or not can be checked every time the blood glucose level is measured. Thus, a blood glucose meter with higher safety can be provided.

Other Embodiments

An embodiment of the present invention has been described above. However, the present invention is not limited to the above-described embodiment, and various modifications can be applied without departing from the gist of the invention.

(A)

In the above embodiment, the liquid crystal display device of the present invention is described as a display section incorporated in a blood glucose meter. However, the present invention is not limited to such an example.

For example, when the present invention is applied as a display section of a variety of analysis devices other than the blood glucose meter, similar effects as described above can be achieved.

(B)

In the above embodiment, when the presence of a defective indication is detected, the appearance of the defective indication is notified to the user by a combination of displaying a message notifying of the appearance of the defective indication, and the buzzer by the alarm section 16. However, the present invention is not limited to such an example.

For example, among these two control operations, only one of them may be performed. Alternatively, the power supply section 17 shown in FIG. 6 may be controlled such that when the appearance of the defective indication is detected, the power supply to the display section 11 is stopped.

In such an example, it is also possible to avoid the user conducting the blood glucose control without noticing that the displayed numerical value is wrong due to the defective indication.

In view of a secure notification to visually handicapped users, it is more preferable to combine a plurality of control operations as in the above-described embodiment.

(C)

In the above-described embodiment, the LCD driver is incorporated within the microcomputer 15. However, the present invention is not limited to such an example.

For example, even when the LCD driver is provided separately from the microcomputer 15, the similar effects as described above can be achieved by using the ports of the LCD driver as the I/O ports.

(D)

In the above-described embodiment, the present invention is applied to the liquid crystal display device of the segment method (the first electrode corresponds to a segmented electrode). However, the present invention is not limited to such an example.

For example, the present invention can also be applied to a liquid crystal display device of a dot matrix method with a relatively small number of dots. In such an example, the first electrode corresponds to a counter electrode formed on a first substrate at a position corresponding to the dots.

INDUSTRIAL APPLICABILITY

The liquid crystal display device of the present invention has effects which enable detection of a defective indication due to an impurity enters into a liquid crystal display panel with a simple structure. Thus, it is applicable not only to liquid crystal display devices of the segment method but also to a wide variety of liquid crystal display devices.

The invention claimed is:

1. A liquid crystal display device, comprising:
    a liquid crystal display panel which includes a first substrate with a first electrode formed thereon, a second substrate with a common electrode formed thereon and a liquid crystal enclosed between the first substrate and the second substrate, and which displays by changing an orientation of the liquid crystal by a difference in potential applied between the first electrode and the common electrode;
    an input and output section which has a first output terminal which sends a signal to the first electrode and a second output terminal which sends a signal to the common electrode configured to drive the liquid crystal display panel;
    a control section which uses the first output terminal and the second output terminal of the input and output section as input and output terminals for a defective indication inspection configured to perform an inspection for a defective indication in the liquid crystal display panel, and which performs the inspection for a defective indication by detecting whether a signal sent from one of the input and output terminals of the input and output section can be received at the other of the input and output terminals and performs the inspection for a defective indication every time power is turned on, and/or the display is switched, and stops supply of electric power to the liquid crystal display panel in response to detection of a defective indication;
    a sensor section protruding outward in a longitudinal direction from a top end of the liquid crystal display device; and
    a sensor located at a distal end of the sensor section connected to the control section configured to contact blood for measurement of blood glucose level in the blood.

2. The liquid crystal display device according to claim 1, wherein the control section displays a message notifying that a defective indication appears on the liquid crystal display panel when the control section detects the defective indication.

3. The liquid crystal display device according to claim 1, wherein the control section sounds an alarm sound when it detects the defective indication.

* * * * *